United States Patent [19]

Girijavallabhan et al.

[11] Patent Number: 5,449,782

[45] Date of Patent: Sep. 12, 1995

[54] ORALLY ACTIVE ANTIVIRAL COMPOUNDS

[75] Inventors: Viyyoor M. Girijavallabhan, Parsippany; Ashit K. Ganguly, Upper Montclair; Richard W. Versace, Wanaque, all of N.J.

[73] Assignee: Schering Corporation, Kenilworth, N.J.

[21] Appl. No.: 287,325

[22] Filed: Aug. 8, 1994

Related U.S. Application Data

[60] Division of Ser. No. 39,532, Mar. 26, 1993, Pat. No. 5,350,772, which is a continuation of Ser. No. 717,451, Jun. 19, 1991, abandoned.

[51] Int. Cl.$^6$ ............... C07D 213/30; C07D 213/55; C07D 213/56; C07D 493/04
[52] U.S. Cl. ............... 546/275; 546/337; 546/339; 546/342
[58] Field of Search ............... 546/339, 337, 342, 275; 568/645

[56] References Cited

U.S. PATENT DOCUMENTS 5,350,772  9/1994  Girijavallabhan et al. ......... 514/721

*Primary Examiner*—Alan L. Rotman
*Attorney, Agent, or Firm*—Thomas D. Hoffman

[57] ABSTRACT

A compound represented by formula I $$Ar_1-O-M-O-AR_2 \qquad I$$

wherein $Ar_1$ and $Ar_2$ are independently substituted phenyl or substituted pyridinyl, the substituents on said phenyl or pyridinyl being independently selected from one, two or three of $(C_1-C_{10})$alkyl, $(C_1-C_{10})$ alkoxy, halogen, carbamyl, $(C_1-C_{10})$ alkoxycarbonyl, oxazoyl, and $(C_1-C_{10})$ alkyl substituted by halogen, $(C_1-C_{10})$ alkoxy, hydroxy, or $(C_1-C_{10})$ alkoxycarbonyl;

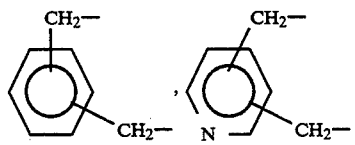

M is
$(C_4-C_8)$ alkylene, $(C_4-C_8)$ alkenylene or $(C_4-C_8)$-alkynylene;
O is oxygen;
or pharmaceutically acceptable salts thereof.

as well as pharmaceutical compositions containing the compounds and methods of treating or preventing viral infections, especially picornaviral infections, are disclosed.

1 Claim, No Drawings

ORALLY ACTIVE ANTIVIRAL COMPOUNDS

This is a division of application Ser. No. 08/039,532 filed Mar. 26, 1993 now U. S. Pat. No. 5,350,772 which is a continuation of Ser. No. 07/717,451 filed Jun. 19, 1991.

BACKGROUND

This invention relates to compounds having antiviral activity, pharmaceutical composition containing these antiviral compounds and methods of treating and in some cases even preventing viral infections, especially picornavirial infections, in mammals using such pharmaceutical compositions.

U.S. Pat. No. 4,851,423 and pending European Patent Application No. 0274867, published Jul. 20, 1988, generally, disclose compounds having antiviral, antiinflammatory and platelet activating factor inhibition activities. The pending European Patent Application discloses such compounds which are represented by the following structural formulas I and II

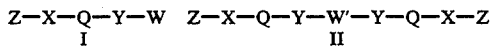

pharmaceutically acceptable acid addition, basic addition, and quaternary amine salts thereof and pharmaceutically acceptable solvates thereof, wherein

- each Z is independently tertiary butyl, phenyl, naphtyly or adamantanyl; substituted phenyl, wherein the substituents are one more of halogen, lower alkoxy, phenoxy, nitrile, nitro, phenylsulfonyl, loweralkylsulfonyl, oxazol-2-yl, lower alkanoyl, benzoyl, lower alkoxycarbonyl, lower alkyl, phenyl, lower alkylthio, phenylaminothiocarbonyl, or lower alkylaminothiocarbonyl; 4 to 6 membered unsubstituted or substituted heterocyclic ring containing at least one nitrogen in the ring with the remaining members of the ring being at least one carbon, and optionally sulfur or oxygen wherein the substituents are one or more or —COOH, —CH$_2$OH, lower alkyl, lower alkylcarbonyl, or aryl lower alkyl;
- X and Y are each independently a bond, —O—, —S—, —SO$_2$—,

- each Q is independently a divalent substituted or unsubstituted, straight or branched chain lower alkanediyl, loweralkanediyl-cycloalkanediyl-lower alkanediyl, lower alkanediyl, lower alkynediyl, phenylene, dihydrofurandiyl,, tetrahydrofurandiyl, tetrahydropyrandiyl, lower alkanediyl-tetrahydrofurandiyl-lower alkanediyl wherein the substituents are one or more of hydroxy, epoxy, fluorine, chlorine, azide, or amino;
- W is a monovalent substituted or unsubstituted aryl group or a heterocyclic single or fused ring containing from 4 to 10 ring atoms, at least one hetero atom of which is a nitrogen, atom and the remaining ring atoms being at least one carbon and optionally sulfur or oxygen, wherein the substituents are one or more of hydroxy, oxo, amino, carbamoyl, carboxyl nitrile, nitro, lower alkyl, lower alkyoxycarbonyl, halogen, sulfamyl, lower alkoxycarbonyllower alkyl, lower alkythio, lower alkoxy, hydroxy lower alkyl, amino lower alkyl, carboxy lower alkyl, guanidino, thioureido lower alkyl sulfonylamino, aminocarbonyllower alkyl, allyloxycarbonylmethyl or carbamoyloxylower alkyl, with the proviso that W cannot be substituted or unsubstituted isoxazolyl, W' is divalent W.

However, the compounds of this invention are not specifically disclosed.

SUMMARY OF THE INVENTION

The present invention provides a compound represented by formula I $$AR_1\text{—O—M—O—}Ar_2 \qquad \text{I}$$

wherein Ar$_1$ and Ar$_2$ are independently substituted phenyl or substituted pyridinyl, the substituents on said phenyl or pyridinyl being independently selected from one, two or three of (C$_1$-C$_{10}$) alkyl, (C$_1$-C$_{10}$) alkoxy, halogen, carbamyl, (C$_1$-C$_{10}$) alkoxycarbonyl, oxazolinyl, and (C$_1$-C$_{10}$) alkyl substituted by halogen, (C$_1$-C$_{10}$)alkoxy, hydroxy, or (C$_1$-C$_{10}$) alkoxycarbonyl;

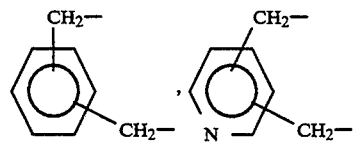

M is
(C$_4$-C$_8$) alkylene, (C$_4$-C$_8$) alkenylene or (C$_4$-C$_8$)alkynylene;
O is oxygen;
or pharmaceutically acceptable salts thereof.

The present invention, in a preferred embodiment, provides a compound represented by formula II or III $$AR_{1a}\text{—O—M—O—}Ar_{1b} \qquad \text{II}$$

$$Ar_{2a}\text{—O—M—O—}Ar_{2b} \qquad \text{III}$$

wherein Ar$_{1a}$ and Ar$_{1b}$ are independently selected from phenyl substituted by one, two or three of (C$_1$-C$_{10}$) alkyl, (C$_1$-C$_{10}$)-alkoxy, halogen, oxazolinyl, carbamyl, (C$_1$-C$_{10}$) alkyl substituted by halogen, (C$_1$-C$_{10}$) alkoxy, hydroxy or (C$_1$-C$_{10}$) alkoxycarbonyl:

Ar$_{2a}$ and A$_{2b}$ are pyridinyl substituted by one, two or three of (C$_1$-C$_{10}$) alkyl, (C$_1$-C$_{10}$) alkoxy, halogen, oxazolinyl, carbamyl, (C$_1$-C$_{10}$)-alkyl substituted by halogen, (C$_1$-C$_{10}$) alkoxy, hydroxy or (C$_1$-C$_{10}$) alkoxycarbonyl;

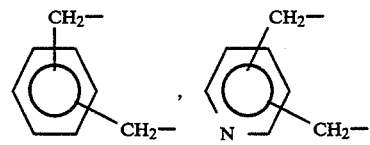

M is
(C$_4$-C$_8$) alkylene
(C$_4$-C$_8$) alkenylene or (C$_4$-C$_8$) alkynylene;
or a pharmaceutically acceptable salt thereof The present invention also provides a pharmaceutical composition for treating viral infections which comprises an antivirally effective amount of a compound of formula I and a pharmaceutically acceptable carrier. Pharmaceutical compositions adapted for oral administration of a compound of this invention are preferred.

The present invention further provides a method of treating a viral infection in a mammal afflicted with a viral infection which comprises administering to such a mammal an antivirally effective amount of a compound of formula I or a pharmaceutically composition containing said compound.

The present invention further provides a method treating or preventing a picornaviral infection in a mammal in need of such treating or preventing which comprises administering to said mammal an antipicornavirally effective amount of a compound of formula I or a pharmaceutical composition containing said compound.

DETAILED DESCRIPTION OF THE INVENTION AND OF THE PREFERRED EMBODIMENTS

We have found that, the compounds of this invention, compared to the prior art compounds, have superior antiviral activity, exhibit oral activity and a broader spectrum of antiviral activity.

The compounds of this invention, have been found to be active against ether-resistant RNA viruses, i.e. picornaviruses which includes enteroviruses and rhinoviruses. The enteroviruses include poliovirus, coxsackieviruses and echoviruses. Rhinoviruses include those viruses associated with the common cold and certain other respiratory ailments. The compounds of this invention have been found to be active against a large numbers of enteroviruses, including poliovirus-2, coxsackieviruses A9, A21 and B1, and Echo 4, 6 and 11. In addition, the compounds of this invention have been found to be active against particular rhinoviruses such as rhinovirus 1A, 1, 14 and 86. The representative compounds of this invention have further been found to exhibit oral activity in the murine poliovirus-encephalitis model. The compounds of this invention may be readily synthesized by simple chemical synthetic steps from commercially or readily available starting materials.

The term "substituted phenyl" means phenyl substituted by one, two or three substituents independently selected from $(C_1-C_{10})$alkyl, $(C_1-C_{10})$ alkoxy, halogen, carbamyl, $(C_1-C_{10})$-alkoxycarbonyl, oxazolinyl, and $(C_1-C_{10})$ alkyl substituted by halogen, $(C_1-C_{10})$ alkoxy, hydroxy, or $(C_1-C_{10})$ alkoxycarbonyl.

Preferred substituted phenyl includes phenyl substituted by two substituents selected from $(C_1-C_{10})$ alkoxy such as methoxy, and ethoxy and halogen such as Cl and F. More preferred substituted phenyl includes phenyl substituted by two of methoxy, chloro and flouro such as

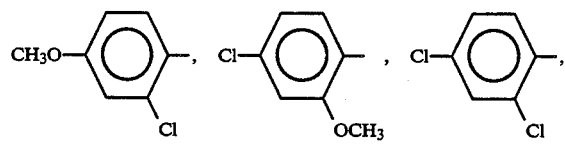

-continued

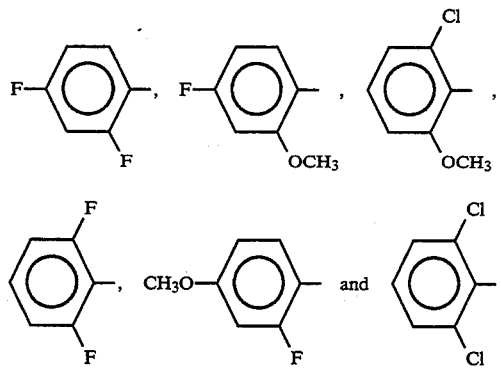

The term "$(C_1-C_{10})$ alkyl" means straight and branched chain alkyl groups of one to ten carbons such as methyl, ethyl, n, and iso-propyl n-iso- sec and tert-butyl, n-, sec, iso, tert- and neo-pentyl, n-, see-, iso, tert and neo-hexyl and the like.

The term "$(C_1-C_{10})$ alkoxy" means straight and branched chain $(C_1-C_{10})$ alkyl groups univaent bonded to divalent oxygen.

The term "halogen" includes flouro-, chloro, bromo, and iodo.

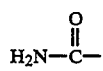

The term "carbamyl" means

The term "$(C_1-C_{10})$ alkoxy carbonyl " mean $(C_1-C_{10})$ alkoxy univalently bonded to carbonyl.

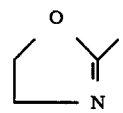

The term "oxazolinyl" means

The term "$(C_1-C_{10})$ alkyl substituted by halogen, $(C_1-C_{10})$alkoxy, hydroxy or $(C_1-C_{10})$ alkoxycarbonyl" includes perhalo $(C_1-C_{10})$ alkyl as well as mono- and dihalosubstituted $(C_1-C_{10})$ alkyl such as fluoromethyl, difluoroethyl and trifluoromethyl; $(C_1-C_{10})$ alkoxy $(C_1-C_{10})$ alkyl such as methoxymethyl, ethoxymethyl, isoproproxymethyl and the like, hydroxy$(C_1-C_{10})$ alkyl such as hydroxymethyl, and hydroxyethyl; and $(C_1-C_{10})$ alkoxycarbonyl substituted $(C_1-C_{10})$ alkyl such as methoxycarbonylmethyl, ethoxycarbonylethyl, isopropoxycarbonylmethyl and tert-butoxycarbonylmethyl.

The term $(C_4-C_8)$alkylene means $—(CH_2)n—$ wherein n is 4 to 8, preferably n is 6 to 8.

The term $(C_4-C_8)$alkenylene means $—(CH_2—)_g—(CH=CH)_h—(CH_2)_i—$ wherein g and i are independently 1 to 5 and h is 1 or 2 including, for example, cis— and trans— $—CH_2CH=CH—CH_2—$, $—CH_2—CH=CH—CH_2CH_2—$ or $—CH_2—CH_2—CH=CH—CH_2—$, $—CH_2CH=CH—CH_2—CH_2CH_2—$, $—CH_2—CH_2—CH=CH—CH_2—CH_2—$, $—CH_2CH_2—CH_2—CH=CH—CH_2—$, $—CH_2—CH=CH—(CH_2)_4—$, $—CH_2CH_2CH=CH—(CH_2)_3—$, $(CH_2)_3—CH=CH—(CH_2)_2—$, $—(CH_2)_4CH=CH CH_2—$, $—CH_2—CH=CH—(CH_2)_5—$, $—CH_2—CH-$ $_2$—CH=CH(CH$_2$)$_4$—,(CH$_2$)$_3$—CH=CH(CH$_2$)$_3$— or —(CH$_2$)$_2$—CH=CH—CH$_2$—.

The term (C$_4$-C$_8$) alkynylene means —(CH$_2$)$_r$—(-C≡C)$_s$—(CH$_2$)$_t$— wherein t and r are 1 to 5, and s is 1 or 2 including for example —CH$_2$—C≡C—CH$_2$—,—(CH$_2$)$_3$—C≡C—CH$_2$—, —CH$_2$—C≡C—CH$_2$CH$_2$—C≡C—CH$_2$—, —(CH$_2$)$_2$—C≡C—(CH$_2$)$_2$—, —CH$_2$—C≡C—(CH$_2$)$_3$—, —(CH$_2$)$_4$—C≡C —CH$_2$—, —(CH$_2$)$_3$—C≡C—(CH$_2$)$_2$—, —(CH$_2$)$_2$—C≡C—(CH$_2$)$_3$—, —CH$_2$—C≡C —(CH$_2$)$_4$—, —(CH$_2$)$_3$—C≡C—CH$_2$—, —(CH$_2$)$_4$—C≡C —(CH$_2$)$_2$, —(CH$_2$)$_3$—C≡C—(CH$_2$)$_3$—, —(CH$_2$)$_2$—C≡C—(CH$_2$)$_4$— or —CH$_2$—C≡C—(CH$_2$)$_5$—.

The compounds of this invention have been found to be active against ether-resistance RNA viruses, i.e. picornaviruses which includes enteroviruses and rhinoviruses. The enteroviruses include poliovirus, coxsackieviruses and echoviruses. Rhinoviruses include those viruses associated with the common cold and certain other respiratory ailments. Over one hundred serotypes are identified. Although the compounds of this invention are not active against all the rhinoviruses, they are active against a large number of them including. The following rhinoviruses 1A, 2, 3, 4, 5 7, 9, 14, 15, 21, 36, 39, 41, 42, 54, 59, 70, 74, 85 and 86. The compounds of this invention are also active against the enteroviruses such as poliovirus-2, Coxsackieviruses A9, A21 and B1, and Echo 4, 6 and 11.

In addition, the compounds of this invention showed activity when tested in in vitro activity assays. The first in vitro antiviral assay performed on the compounds of the invention is plaque reduction assay which measures the ability of compounds to neutralize virus infectivity, e.g. picornavirus infectivity. In tests against poliovirus -2, the IC$_{50}$ values of the compounds of this invention were about 0.008 to about 2.0 microgram/ml. The IC$_{50}$ value in all antiviral tests is the concentration of test compound in micrograms per milliliter "μg/mL" which results in a 50% decrease in plaque forming units compared to a non-treated control.

The second in vitro antiviral assay performed was a modified, premix plaque reduction assay wherein the virus and test compound are mixed and incubated at 37° C. for 1 hr prior to overlaying with an agar medium. The active compounds of this invention had IC$_{50}$S in this modified premix plaque reduction assay, of from about 0.01 to about 3.0 microgram/mL against poliovirus 2, about 0.05 to about 5 microgram/mL against human rhinovirus 3 and about 0.8 to 5 microgram/mL against cosackievirus A9.

The plaque reduction assay performed as disclosed by Woods, M. G. et al., *Antimicrob Agent Chemother* (1989) Vol. 3, p 2069–2074 involves overlaying HeLa cells with agar medium containing measured concentrations of the test compound following virus absorption, then incubating for 72 hours. The resulting plaques are stained, visualized and measured to determine direct virus growth inhibition as evidenced by plaque reduction with compared to a control.

The modified premix plaque reduction assay measures the capability of a compound to directly inactivate the virus itself and is considered more sensitive because of its ability to discriminate more clearly the virus growth neutralizing effects between compounds whose IC$_{50}$S are close according to the standard plaque reduction assay as disclosed by Woods et al.

The compounds of this invention were tested for antiviral activity in (1) primary in vitro assays with poliovirus -2 by measuring thermal stability, MTT antiviral activity, MTT cytotoxicity therapeutic index and premix plaque reductions (2) MTT- based assays with entroviruses such as Echo 4,6 and 11 and Coxsackieviruses A21, B1 and A9 (3) in HeLa cell viability and (4) in an in vivo murine poliovirus-encephalitis model.

Based on these tests, the preferred antiviral compounds represented by the following structural formulas Ia to If were identified:

| Compound | Ar$_1$ | M | Ar$_2$ |
|---|---|---|---|
| Ia | CH$_3$O—(phenyl, Cl)— | —CH$_2$—(phenyl)—CH$_2$— | —(phenyl, Cl)—OCH$_3$ |
| Ib | " | —(CH$_2$)$_6$— | " |
| Ic | " | —CH$_2$—(pyridyl, N)—CH$_2$— | " |
| Id | " | —CH$_2$\C=C/CH$_2$— (cis, H/H) | " |
| Ie | " | —CH$_2$C≡CCH$_2$— | " |

-continued

| Compound | Ar₁ | M | Ar₂ |
|---|---|---|---|
| If | " |  | 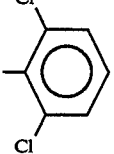 |

The compounds of formulas Ia–If in the primary screen against (1) poliovirus-2 have $IC_{50}$ thermal stabilities of $<10$ μg/mL; (b) Therapeutic Indices of (MTT Cytotoxicity/MTT Antiviral) of $>50$; (c) premix plaque reduction values of $<10$ μg/mL (2) $IC_{50}$ values of $<5.0$ μg/mL for 70% of the enteroviruses; (3) $IC_{50}$ values of $<50$ μg/mL against in the HeLa cell viability model after 24 hrs and (4) showed oral activity in the in-vivo murine poliovirus-encephaltis model.

The thermal stability test model is a measure of the capability of a compound to interact with the vital capsid to alter its characteristics, and thus to inactivate it and to render it incapable of inducing infection. The thermal stability test was run as described by Tisdale, M. et al. in the *J. Antimicrob. Chemother* (1984) Vol. 14, Suppl A, 97–105.

The MTT antiviral and the MTT cytotoxicity assays were based on poliovirus-2 cells propagated and titered in HeLa cells in accordance with the procedure of Mosmann, T., *J. Immunological Methods* (1983), Vol. 65, 55–63.

The MTT antiviral assay measures the capability of a virus to infect and destroy tissue culture cells in vitro.

The MTT cytotoxicity test measures the capability of a chemical synthetic compound to destroy cells, rendering the cells incapable of supporting viral replication in vitro.

The Therapeutic Index is the ratio of the MTT cytotoxicity to the MTT antiviral activity in HeLa cells based on antiviral assay with a virus, e.g. the poliovirus −2 after 24hr.

The $IC_{50}$ value for the compounds of this invention is determined by measuring the concentration of the compound which inhibits 50% of virus growth without destroying the tissue culture cells in vitror, endering these cells incapable of supporting growth.

The oral murine poliovirus-encephalites mode was measured using a solution of the compound in, for example, corn oil or a colloidal suspension of the compound in corn oil in accordance with the procedure of McKinlay, M. A., et al. *Antimicrob Agents Chemother*, (1986) Vol. 29, 30–32.

The compounds of this invention may be administered by any conventional mode of administration by employing and antiviral effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 1.0 to about 1000 mg/kg of body weight per day may be administered to provide antiviral activity. For example, when administered orally doses of from about 2 to about 200 mg/kg of body weight may be used; and when administered parenterally, e.g., intravenously, dosages of from about 0.1 to about 20 mg/kg body weight may be used.

When administered topically, the amount of compound administered varies widely with the amount of skin being treated, as well as with the concentration of active ingredient applied to the affected area.

The compounds of the invention may also be deliverable transdermally for systemic distribution. The transdermal compositions can take the form of creams, lotions and/or emulsions and can be included in transdermal patch of the matrix or reservoir type as are conventional in the art for this purpose.

For the preferred oral administration, the compounds of the invention are typically formulated in the form of tables, capsules, elixirs, solutions, suspensions and the like preferably solutions. For parenteral administration, they may be formulated into solutions or suspensions. Topical formulations such as lotions, creams, ointments, sprays and mechanical delivery devices, e.g. transdermal can also be made with the compounds of this invention.

Typical pharmaceutically acceptable carriers for use in the formulations described above are exemplified by: sugars such as lactose, starches such as corn starch, cellulose, and derivatives such as sodium carboxymethyl cellulose, ethyl cellulose and methyl cellulose; and other carriers well known in the art. The compositions may also contain preservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, e.g. the age and weight of the individual being treated, the mode of administration, the potency of the administered compound, the indication for which the drug is administered and the severity of the ailment being treated.

Typically, the dosage administered per day for treating viral infections will be oral administration of from about 2 mg/kg to about 200 mg/kg daily in single of divided doses, with about 5 mg/kg to about 60 mg/kg preferred.

The compounds of this invention represented by formula I are prepared by reaction Schemes A and B using commercially available starting materials and simple chemical reactions.

Scheme A

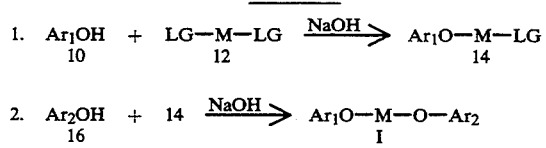

Phenol 10, e.g. 2-chloro-4-methoxyphenol is reacted with compound 12 wherein LG is a leaving group such as Br, I, mesylate or tosylate in the presence of an alkali metal hydroxide such as NaOH. The reaction takes place at a temperature of about −20° C. to 60° C. in an inert, organic solvent such as dimethylsulfoxide (DMSO), dimethyl formamide (DMF) or tetrahydrofuran (THF). Compounds of formula 14 are isolated by addition of water and the crude product is purified by crystallization and/or column chromatography. Compound 14 is reacted with phenol 16 under reaction conditions similar to those employed in step 1 to produce compound of formula I. Scheme A is employed wherein compounds 10 and 16 are different. In the cases wherein compounds 10 and 16 are identical, Scheme B is used.

Scheme B

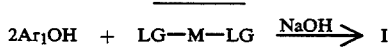

The structural formulas of the compounds of the Examples were determined by analysis of PNMR and mass spectra.

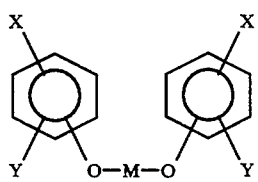

TABLE I

| Example | X | Y | M |
|---|---|---|---|
| 1 | 2-Cl | 4-CH$_3$O | —(CH$_2$)$_6$— |
| 2 | " | " | —(CH$_2$)$_5$— |
| 3 | ' | ' | —(CH$_2$)$_7$— |
| 4 | " | " | —CH$_2$—C≡C—CH$_2$— |
| 5 | " | " | H\\C=C/CH$_2$— / —CH$_2$/ \\H |

EXAMPLE 1

Add 2 g of 6-(2-chloro-4-methoxyphenoxy)hexyl-1-iodide (prepared in accordance with the procedures of Example 2 (a) of V. M. Girijavallabhan et al in U.S. Pat. No. 4,851,423 issued Jul. 25, 1989 and Diana et al. in J. Med Chem (1985) Vol. 28 p 748–52) to a mixture of 2g of 2-chloro-4-methoxyphenol and 0.05 g of NaOH in 10 mL of DMF. Stir the so-formed reaction mixture overnight. Partition the reaction mixture with CH$_2$Cl$_2$ and water. Separate the organic phase and evaporate the solvent to obtain a crude product. Purify the crude product on a silica gel chromatography column by eluting with 100% CH$_2$Cl$_2$ to provide 1.29 g of 1,1'-[1,6-hexanediyl bis(oxy)]bis-[2-chloro-4-methoxybenzene]

EXAMPLE 2

Use the procedure of Example 1 except substituent an equivalent amount of 5-[2-chloro-4-methoxyphenoxy]-pentyl-1-iodide [prepared in accordance with Example 16(a) of U.S. Pat. No. 4,851,423] for the hexyl-1-iodide of Example 1.

EXAMPLE 3

Use the procedure of Example 1 except substitute an equivalent amount of 5-[2-chloro-4-methoxyphenoxy)-heptyl-1-iodide [prepared in accordance with Example 15(a) of U.S. Pat. No. 4,851,423] for the hexyl-1-iodide of Example 1.

EXAMPLE 4

Add 1.23 g of 1,4-dichlorobutyne-2 to a mixture of 3.5 g of 2-chloro-4-methoxyphenol and 1.8 g of a 50:50 (w/w) mixture of NaOH:H$_2$O in 30 mL of DMF. Stir the so-formed mixture overnight at room temperature. Purify the crude product in accordance with the procedure of Example 1 to provide 1,1'-[-1,4-butyne-2-diyl bis(oxy)]bis-[2-chloro-4-methoxybenzene]

EXAMPLE 5

Add 2.14 g of trans -1,4-dibromobutene-2 to a mixture of 3.5 g of 2-chloro-4-methoxyphenol and 1.8 g of a 50:50 (w/w) mixture of NaOH:H$_2$O in 30 mL of DMF. Stir the so-formed mixture overnight at room temperature. Purify the crude product in accordance with the procedure of Example 1 to provide 1,1'-[1,4-trans-butene-2-diyl bis(oxy)]bis-[2chloro-4-methoxybenzene].

EXAMPLES 6–14

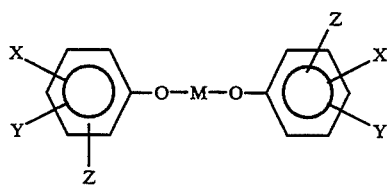

TABLE

| Example No. | X | Y | Z | M |
|---|---|---|---|---|
| 6 | 2-Cl | 4-CH$_3$O | H | 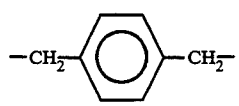 |
| 7 | 2-Cl | 6-Cl | H | 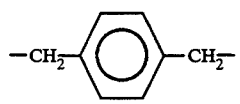 |
| 8 | 2-Cl | 4-CH$_3$ | H | 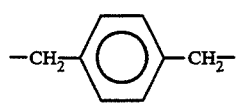 |
| 9 | 2-F | 4-F | H | 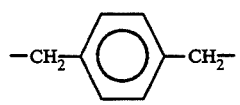 |

TABLE-continued

| Example No. | X | Y | Z | M |
|---|---|---|---|---|
| 10 | 2-Cl | 5-CH3 | H | −CH2−〈ph〉−CH2− |
| 11 | 2-Cl | 4-CH3 | H | −CH2 / −CH2− (meta-xylylene) |
| 12 | 2-Cl | 4-CH3 | H | −CH2−〈ph〉−CH2− |
| 13 | 2-Cl | 4-CH3— | 5-CH3— | " |
| 14 | H | O | H | " |

(Example 14, Y = morpholino group)

EXAMPLE 6

To a stirred mixture of 10.0 g of 2-chloro-4-methoxyphenol and 2.5 g of NaOH in 50 mL of DMF add 7.0 g of α,α'-dibromo-p-xylene and stir the so-formed reaction mixture at room temperature for 4 hrs. Add 300 mL of water and filter the crude precipitated solid. Purify the crude product by re-crystallization from the methylene chloride to produce 9.12 g of 1,1'-[1,4-phenylene bis(methylenoxy)]-bis [2-chloro-4-methoxybenzene] as a pure compound.

EXAMPLES 7–14

Follow the procedure of Example 3 except substitute the appropriate substituted phenol for 2-chloro-4-methoxyphenol and the appropriate dibromide for α,α'-dibromo-p-xylene to provide the corresponding product.

EXAMPLE 15

VI

| Example | W | V | M | X | Y |
|---|---|---|---|---|---|
| 15 | 4-CH3O— | 2-Cl | 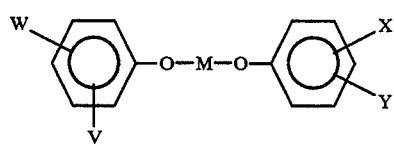 | 2-Cl | 6-Cl |

EXAMPLE 15

A. Add 5 g of 2-chloro-4-methoxyphenol to a mixture of 17 g of α,α-dibromo-p-xylene to a stirred mixture of 2.5 g of 50:50 (w/w) NaOH:H2O and 50 mL of DMF. Stir the so-formed mixture for 4 hours. Partition the reaction mixture with methylene chloride and water. Separate the organic layer and remove the solvent by rotary evaporation to obtain a solid residue. Purify the residue on a silica gel chromatography column using pure hexane to pure methylene chloride as the eluants to provide 8 g of 1-[4-α-bromomethylbenzyl]-2-chloro-4-methoxyphenol.

B. To a solution of 0.50 g of 2,6-dichlorophenol in a mixture of 0.12 g of NaOH in 5 mL of DMF, add 0.50 g of the phenol from Example 15A and stir for 4 hours at room temperature. Add 50 mL of water to the reaction mixture and filter the crude precipitate so-formed. Purify the crude precipitate by crystallization from methylene chloride to provide 350 mg of 2-chloro-1-[[4-[(2,6-dichlorophenoxy)methyl]phenyl]methoxy]-4-methoxybenzene as a pure solid.

EXAMPLES 16–17

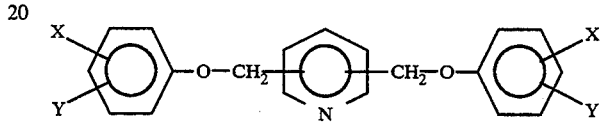

TABLE

| Example No. | X | Y | −CH2−〈pyridine〉−CH2− |
|---|---|---|---|
| 16 | 2-Cl— | 4-CH3O— | 2,5-pyridinediylbismethylene |
| 17 | 2-Cl— | 4-CH3O— | 2,6-pyridinediylbismethylene |

EXAMPLE 16 a) Add 50 mL of thionyl chloride to 25 g of pyridine-2,5-dicarboxylic acid and heat the so-formed mixture at reflux for 6 hrs. Remove all volatiles by vacuum distillation to obtain crude di acid chloride. Immerse flask contain diacid chloride in an ice-batch and add 100 mL of absolute ethanol thereto. Slowly add 30 mL of triethlamine to the stirred reaction mixture and continue stirring for ½ hr. Add Ethyl acetate/water to stirred reaction mixture and separate the organic layer. Remove the solvent to produce crude product. Re-crystallize crude product from hexane/methylene chloride to give 25 g of the pyridine-2,5-bis (ethylcarboxylate).

b) Slowly add 9 g of NaBH4 to a solution of the diester from step (a) in 150 mL of ethanol. Add 13.5 g of CaCl2 as solution in 150 mL of ethanol to the stirred reaction mixture and continue stirring the so-formed reaction mixture overnight. Add 12 g of H2SO4 and filter off the so-formed solid. Add HCl to adjust to the pH of the solution to about 4. Remove all solvent by rotatory evaporation to produce a crude product. Purify the crude product by crystallization from methanol to produce 11 g of 2,5-bis[hydroxymethyl]-pyridine as the HCl salt.

c) To a solution of 10 g of the pyridine compound of 16b and 32 mL (4 eq) of triethylamine in 250 mL of methylene chloride in a reaction vessel immersed in an ice bath. Add thereto 11 mL (2.5 eq) of CH3SO2Cl via a syringe pump. Stir the so-formed reaction mixture for ½ hr after the addition was complete. Partition with methylene chloride and water. Separate the organic layer and remove the solvent to give a crude product which was purified by crystallization from methylene chloride hexane to give 2,5-pyridinediyl bis(methylene mesylate)

d) Follow the procedure of Example 6 except substitute for αα'-dibromo-p-xylene an equivalent quantity of the bis mesylate of Example 16 (c) to give 1,1 '-[2,5-pyridinediyl bis (methyleneoxy)]bis-[2-chloro-4 -methoxybenzene] as a pure solid.

EXAMPLE 17

Follow the procedure of Example 16 except substitute an equivalent quantity of 2,6-pyridinedicarboxylic acid in step(a) to provide in step (d) 2.1 g of 1,1 '-[2,6-pyridinediyl bis(methyleneoxy)]bis-[2-chloro-4-methoxybenzene] as a pure solid.

EXAMPLES 18–20

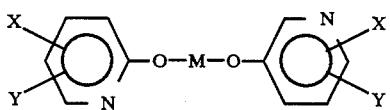

VII

| Example No. | X | Y | M |
| --- | --- | --- | --- |
| 18 | 2-Cl | H | —CH₂—⟨pyridine⟩—CH₂— |
| 19 | 4-CH₃ | H | " |
| 20 | 2-NH₂—C(=O) | H | " |

Follow the procedure of Example 6 except substitute an equivalent amount of the appropriate 3-hydroxypyridine for 2-chloro-4-methoxyphenol to provide the corresponding compound.

EXAMPLES 21–23

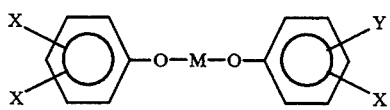

VIII

| Example No. | X | Y | M |
| --- | --- | --- | --- |
| 21 | 2-Cl | 4-CO₂Et | —CH₂—⟨phenyl⟩—CH₂— |
| 22 | 2-Cl | 4-HOCH₂— | " |
| 23 | 2-Cl | 4-CH₃OCH₂— | " |

EXAMPLE 21

Follow the procedure of Example 6 except add 6 g of α-α'-dibromo p-xylene and substitute 10.0 g of 2-chloro-4 ethoxycarbonyl phenol for 2-chloro-4-methoxyphenol to obtain 6.8 g of 1,1'-[1,4-phenylene bis(methyleneoxy)]-bis-[2-chloro-4-ethoxycarbonylbenzene].

EXAMPLE 22

Reduce 5 g of the compound of Example 21 with a solution of 15 mL of 1 molar LiALH₄ in THF at 0° C. Stir the so-formed reaction mixture for 6 hrs. Add thereto 20 mL of a saturated aqueous solution of NH₄Cl and filter off the solids. Remove the solvent from the filtrate to produce a crude product. Purify the crude product by crystallization from CH₂Cl₂ to produce 3.6 g of 1,1 '[1,4-phenylene bis(methyleneoxy)]-bis-[2-chloro-4-phenylmethanol].

EXAMPLE 23

To the 1 g of the compound of Example 22 slowly add 5.25 mL of NaN[(Si(CH₃)₃]₂. Stir the so-formed reaction mixture for 15 minutes. Add thereto 0.33 mL of CH₃ I(neat) and stir the so-formed reaction mixture for 4 hours. Add thereto 200 mL of H₂ O and collect the crude product by filtration. Purify the crude product by crystallization from CH₂Cl₂ and hexane to produce 750 mg of 1,1'-[1,4-phenylene bis (methyleneoxy)]-bis-[2-chloro-4-(methoxymethyl)benzene]

What is claimed is:

1. A compound represented by formula II or III $$AR_{1a}—O—M—O—Ar_{1b} \quad \text{II}$$

$$Ar_{2a}—O—M—O—Ar_{2b} \quad \text{III}$$

wherein Ar₁ₐ and Ar₁ᵦ are independently selected from phenyl substituted by one, two or three of (C₁–C₁₀) alkyl, (C₁–C₁₀) alkoxy, halogen, carbonyl and (C₁–C₋₁₀) alkyl substituted by halogen, hydroxy, (C₁–C₁₀) alkoxy or (C₁–C₋₁₀) alkoxycarbonyl and a single 2-oxazolinyl substituent;

A₂ₐ and A₂ᵦ are pyridinyl substituted by one, two or three of (C₁–C₁₀) alkyl, C₁–C₁₀)-alkoxy, halogen, carbamyl, and (C₁–C₁₀) alkyl substituted by halogen, (C₁–C₁₀) alkoxy, hydroxy, or (C₁–C₁₀) alkoxycarbonyl and a single 2-oxazolinyl substituent;

M in formulas II and III is

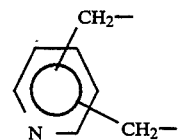

O is oxygen;

or a pharmaceutically acceptable salt thereof.

* * * * *